United States Patent [19]

Du

[11] Patent Number: 5,618,791
[45] Date of Patent: Apr. 8, 1997

[54] MEMORY ENHANCING PEPTIDES

[75] Inventor: Yu-Cang Du, Shanghai, China

[73] Assignee: Shanghai Institute of Biochemistry, Shanghai, China

[21] Appl. No.: 102,896

[22] Filed: Aug. 6, 1993

[30] Foreign Application Priority Data

Aug. 8, 1992 [CN] China .................. 92108527.3

[51] Int. Cl.$^6$ .................. A61K 38/07; A61K 38/08
[52] U.S. Cl. .................. 514/17; 514/18; 514/807; 530/315; 530/330
[58] Field of Search .................. 514/12, 15, 18, 514/807, 17; 530/315, 330

[56] References Cited

U.S. PATENT DOCUMENTS

| | | | |
|---|---|---|---|
| 4,410,511 | 10/1983 | de Wied et al. | 424/177 |
| 4,487,765 | 12/1984 | de Wied | 424/177 |
| 4,593,017 | 6/1986 | de Wied | 514/16 |
| 4,623,640 | 11/1986 | de Wied | 514/18 |
| 5,112,947 | 5/1992 | Masaki et al. | 530/329 |

FOREIGN PATENT DOCUMENTS 0393934 10/1990 European Pat. Off. .

OTHER PUBLICATIONS

Gregoriadis et al (1993) Trends in Biotech.11:440–442.
Harlow et al (1988) "Antibodies:A Laboratory Manual", Cold Spring Harbor Laboratory Press, Cold Spring Harbory N.Y., pp. 660–661 and 667.
Sahgal (1987) Psychopharmacology 93(2): 243–249.
Engelmann et al (1992) Neurosci Lett. 142:69–72.
Chemical Abstracts 118(17): 161345m, vol. 17, No. 2–3, 1992.
Chemical Abstracts 113(9): 71509K, vol. 53, No. 3, 1990.
C. Lin, R. Liu & Y. Du, Cysteinyl Methyl Ester of AVP (4–8), a Potent Agonist on the Maintenance of Passive Avoidance in Rats, Peptides, vol. 11, pp. 633–639, 1990.

A Major Metabolite of Arginine Vasopressin in the Brain is a Highly Potent Neuropeptide, Science, vol. 221, pp. 1310–1312, J.P.H. Burbach, G.L. Kovacs, D. De Wied.
Behavioural Actions of Neurohypophysial Peptides, Proc. R. Soc. Lond. B. 210, 183–195 (1980), D. De Wied.
Vasopressin Antagonists Block Peripheral as Well as Central Vasopressin Receptors, Pharmacology Biochemistry & Behavior, vol. 21, pp. 393–400, 1984, D. De Wied, O. Gaffori, J. M. Van Ree & W. DeJong.
Central Target For The Behavioural Effects of Vasopressin Neuropeptides, Nature vol. 308, (1984), pp. 276–278, D. De Wied, O. Gaffori, J. M. Van Ree & W. de Jong.
Structure Activity Relationship Studies With C–Terminal Fragments of Vasopressin and Oxytocin On Avoidance Behaviors of Rats, The Journal of Pharmacology and Experimental Therapeutics, vol. 241, pp. 268–274, D. De Wied, O. Gaffori, J.P.H. Burbach, G.Kovacs, J. VanRee.
Neonatal Administrations of a Vasopressin Analog (DDAVP) and Hypertonic Saline Enhance Learning Behavior in Rats, Peptides, vol. 9, pp. 717–721, (1988), X. Chen, Z. Chen, R. Liu & Y. Du.

Primary Examiner—Marian C. Knode
Assistant Examiner—Patricia A. Duffy
Attorney, Agent, or Firm—Jacobson, Price, Holman & Stern, PLLC

[57] ABSTRACT

The invention is a class of memory enhancing peptides having the general formula:

$$R_1\text{—Asn—}X_1\text{—}X_2\text{—}X_3\text{—}R_2$$

where
$R_1$=pyroglutamyl, acetyl, H, peptidyl
$X_1$=Ala, Ile, Leu, Tyr, Phe, Val, Trp, Cyt, Hme
$X_2$=Pro, Leu, Ile, Val provided that when $X_2$ is Pro, $X_1$ is not Cyt or Ala;
$X_3$=Arg
$R_2$=OH, $NH_2$, $OR_3$, glycyl
and
$R_3$=$C_{1-6}$ alkyl.

13 Claims, No Drawings

MEMORY ENHANCING PEPTIDES

The invention is a class of memory enhancing peptides (MEPs) related to the C-terminal portion of arginine vasopressin (AVP), a neurohypophyseal hormone.

It has been reported that the administration of AVP retarded the extinction of active or passive avoidance responses in adult rats, but had no effect on its acquisition. As an endocrinic hormone, AVP regulates blood pressure through vasoconstriction and stimulates the reabsorption of water in the distal tubules of the kidney, leading to a concentration of urine. Thus, AVP is not suitable for clinical use for treatment of memory loss.

It has been found that peptides comprising the six C-terminal amino acid residues of AVP or derivatives thereof often exhibit memory enhancing effects when administered to animals, which peptides are as potent or more potent than AVP. These memory effects may occur without the undesirable side effects of elevated blood pressure or antidiuretic activity.

The present invention builds on the state of the art by providing METs of the following formula:

$$R_1—Asn—X_1—X_2—X_3—R_2$$

Asn=asparaginyl $R_1$=pyroglutamyl, acetyl, H, peptidyl (e.g., acetyltyrosylglutaminyl)

$R_2$=OH, $NH_2$, $OR_3$, glycyl $R_3=C_{1-6}$ alkyl $X_1$=alanyl (Ala), isoleucyl (Ile), leucyl (Leu), tyrosyl (Tyr), phenylalanyl (Phe), valyl (Val), tryptophanyl (Trp), cystinyl (Cyt), homomethionyl (Hme)

$X_2$=prolyl (Pro), leucyl (Leu), isoleucyl (Ile), valyl (Val) provided that when $X_2$ is prolyl (Pro), $X_1$ is not Cyt or Ala;)

$X_3$=arginyl (Arg), lysyl (Lys)

Each optically active amino acid residue may be in either the D or L enantiomeric configuration.

Neonatal pretreatment with MEPs of the invention not only improved memory processes in mature animals, but also facilitated memory acquisition in immature individuals. The lowest effect dosages of MEPs of the invention are usually less than that of AVP, and frequently, MEPs of the invention exhibit potencies 10–100 times that of AVP. None of the MEPs of the invention showed significant pressor or antidiuretic side effects even at doses $10^3$ times the effective dose for AVP. Accordingly, it is anticipated that MEPs of the invention will provide a basis for the development of pharmaceutical products for the development of intelligence in youths and to enhance memory, treat amnesia including Alzheimer's disease in adults.

The MEPs of the invention may be prepared by chemical synthesis using conventional solution or solid-phase peptide synthesis methods. To improve the total yield, 3,4-dihydro-3-hydroxy-4-oxo-1,2,3-benzotriazine (BTA) is used as an additive for DCC coupling. Crude synthetic MEPs may be treated with hydrogen fluoride (HF), ammonia/methanol or acetic anhydride separately. All MEPs were isolated and purified by gel filtration on silica gel or sephadex or both followed by HPLC. Purified products were subjected to amino acid analysis and analytical HPLC.

Biological activities of MEPs of the invention are confirmed by bioassay. Blood pressure measurements and urine output measurements were performed on adult rats after intravenous administration of MEPs under ether anesthesia. Passive avoidance behavior of adult rats was carried out in a step-through one trial learning test in a shuttle box, and brightness discrimination tests were performed in a radiant Y maze. Rats neonatally administered with MEPs of the invention were trained during an immature period and subsequently tested as adults.

PREPARATION OF MEPs

MEPs of the invention were prepared according to the following synthetic scheme:

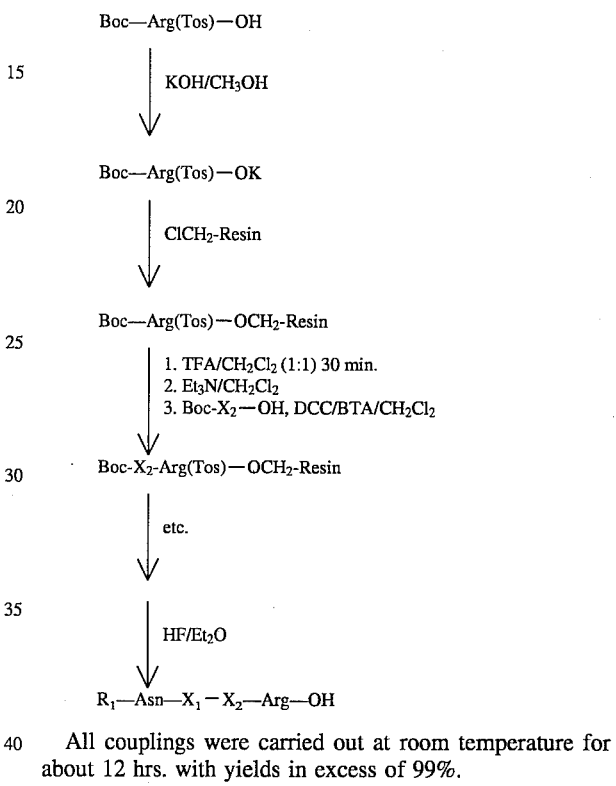

All couplings were carried out at room temperature for about 12 hrs. with yields in excess of 99%.

ASSAY OF BIOLOGICAL FUNCTIONS

MEPs of the invention do not show a significant increase in blood pressure in adult rats receiving an intravenous administration of 20 µg/kg body wt. of peptide.

The inhibition of urine flow rate in hydrated adult rats has been recorded as antidiuretic activity. MEPs of the invention do not cause a detectable positive response by intravenous injection below the dose of 0.4 µg/kg body wt.

Memory enhancing responses were assessed by two kinds of behavioral records, i.e., passive avoidance response of adult rats in a shuttle box and the performance in a radiant Y maze in the acquisition and retention of brightness discrimination of rats neonatally administered. The results are set out in Table I. All MEPs of the invention show significant positive behavioral responses when rats have received a subcutaneous administration of MEP within the dosage range 1 ng–1 µg per animal. MEPs of the invention show a memory enhancing potency 10–100 times that of AVP.

To assess the criticality of the prolyl residue at position $X_2$, the peptide ZNC(C)LR was synthesized, where C(C) is cystinyl and L is leucyl, and its memory enhancing properties were assayed and compared to the known AVP fragment ZNC(C)PR. As seen in Table I, these two peptides have comparable activity indicating that the prolyl residue $X_2$ need not be conserved.

TABLE I

| MEP | Passive Avoidance ng/200 g body wt. adult rat effective dose |
|---|---|
| ZNLPR | 10 |
| (Sequence Id. No. 1) | |
| ZN(Hme)PR | 10–100 |
| (Sequence Id. No. 2) | |
| NAPR | 30 |
| (Sequence Id. No. 3) | |
| NLPR | 3–10 |
| (Sequence Id. No. 4) | |
| AcNLPR—NH$_2$ | 3–10 |
| AVP | 300–1000 |
| ZNC(C)PR | 30–100 |
| (Sequence Id. No. 5) | |
| ZNC(C)LR | 30–100 |
| (Sequence Id. No. 6) | |

Z = pyroglutamyl

TABLE I-continued

| MEP | Passive Avoidance ng/200 g body wt. adult rat effective dose |
|---|---|

Ac = acetyl
N = Asn
L = Leu
P = Pro
R = Arg
A = Ala
C = Cys
C(C) = Cyt
Hme = Homomethionine (S-methylcysteine)

Additionally, oral administration of NLPR to adult rats at a dose of 20 μg/kg/day for 30 days produced a positive brightness discrimination assay.

TOXICITY

MEPs were found to be non-toxic when administered by iv to mice at doses up to 5 mg/kg body wt.

I claim:

1. A memory enhancing peptide of the formula:

$$R_1-Asn-X_1-X_2-X_3-R_2$$

where

Asn=asparaginyl $R_1$=pyroglutamyl, acetyl, H, peptidyl $R_2$=OH, $NH_2$, $OR_3$, glycyl, $R_3$=$C_{1-6}$ alkyl $X_1$=alanyl (Ala), isoleucyl (Ile), leucyl (Leu), tyrosyl (Tyr), phenylalanyl (Phe), valyl (Val), tryptophanyl (Trp), cystinyl (Cyt) homomethionyl (Hme)

$X_2$=prolyl (Pro), leucyl (Leu), isoleucyl (Ile), valyl (Val) provided that when $X_2$ is prolyl (Pro), $X_1$ is not Cyt or Ala;

$X_3$=arginyl (Arg)

and each optically active amino acid residue may be in either the D or L enantiomeric configuration.

2. The peptide as claimed in claim 1, wherein
$R_1$=pyroglutamyl,
$X_1$=Leu,
$X_2$=Pro, and
$X_3$=Arg
$R_2$=OH.

3. The peptide as claimed in claim 1, wherein
$R_1$=H,
$X_1$=Leu,
$X_2$=Pro, and
$X_3$=Arg
$R_2$=OH.

4. The peptide as claimed in claim 1, wherein
$R_1$=acetyl,
$X_1$=Leu,
$X_2$=Pro, and
$X_3$=Arg
$R_2$=$NH_2$.

5. The peptide as claimed in claim 1, wherein
$R_1$=H,
$X_1$=Ile,
$X_2$=Pro, and
$X_3$=Arg
$R_2$=OH.

6. The peptide as claimed in claim 1, wherein
$R_1$=H,
$X_1$=Val,
$X_2$=Pro, and
$X_3$=Arg
$R_2$=OH.

7. The peptide as claimed in claim 1, wherein
$R_1$=H,
$X_1$=Tyr,
$X_2$=Pro, and
$X_3$=Arg
$R_2$=OH.

8. The peptide as claimed in claim 1, wherein
$R_1$=H,
$X_1$=Trp,
$X_2$=Pro, and
$X_3$=Arg
$R_2$=OH.

9. The peptide as claimed in claim 1, wherein
$R_1$=H,
$X_1$=Phe,
$X_2$=Pro, and
$X_3$=Arg
$R_2$=OH.

10. The peptide as claimed in claim 1, wherein
$R_1$=H,
$X_1$=Hme,
$X_2$=Pro, and
$X_3$=Arg
$R_2$=OH.

11. The peptide as claimed in claim 1, wherein the optically active amino acids are in the L enantiomeric configuration.

12. A memory enhancing peptide of the formula:

$$ZNC(C)LR$$

where

Z=pyroglutamyl,

N=Asn,

C(C)=Cyt,

L=Leu, and

R=Arg.

13. A pharmaceutical composition comprising a therapeutically effective amount of the peptide of claim 1 and a pharmaceutically acceptable carrier.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:1:

Glx    Asn    Leu    Pro    Arg
1                           5

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
( A ) NAME/KEY: Homomethionine Peptide
( B ) LOCATION: (2   3)

( x i ) SEQUENCE DESCRIPTION: SEQ ID NO:2:

Glx    Asn    Xaa    Pro    Arg (2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:3:

Asn Ala Pro Arg
    1

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:4:

Asn Leu Pro Arg
    1

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Cystinyl Peptide
        (B) LOCATION: (2 3)

(xi) SEQUENCE DESCRIPTION: SEQ ID NO:5:

Glx Asn Xaa Pro Arg
    1                   5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (  i  i  ) MOLECULE TYPE: peptide (  i  i  i  ) HYPOTHETICAL: NO (  i  v  ) ANTI-SENSE: NO (  v  ) FRAGMENT TYPE: C-terminal (  i  x  ) FEATURE:
    ( A ) NAME/KEY: Cystinyl Peptide
    ( B ) LOCATION: (2   3)

(  x  i  ) SEQUENCE DESCRIPTION: SEQ ID NO:6:

```
Glx  Asn  Xaa  Leu  Arg
 1                    5
```